(12) United States Patent
Dornberger et al.

(10) Patent No.: US 9,392,989 B2
(45) Date of Patent: Jul. 19, 2016

(54) MAMMOGRAPHY APPARATUS

(71) Applicant: Siemens Aktiengesellschaft, Munich (DE)

(72) Inventors: Susanne Dornberger, Erlangen (DE); Thomas Mertelmeier, Erlangen (DE); Ralf Nanke, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 175 days.

(21) Appl. No.: 14/451,737

(22) Filed: Aug. 5, 2014

(65) Prior Publication Data

US 2015/0036796 A1 Feb. 5, 2015

(30) Foreign Application Priority Data

Aug. 5, 2013 (DE) .................... 10 2013 215 376

(51) Int. Cl.
*A61B 6/04* (2006.01)
*A61B 6/00* (2006.01)
*A61B 6/02* (2006.01)

(52) U.S. Cl.
CPC . *A61B 6/54* (2013.01); *A61B 6/025* (2013.01); *A61B 6/0414* (2013.01); *A61B 6/4028* (2013.01); *A61B 6/502* (2013.01); *A61B 6/544* (2013.01)

(58) Field of Classification Search
CPC ......... A61B 6/54; A61B 6/502; A61B 6/0414
USPC ........................................... 378/37
See application file for complete search history.

(56) References Cited

U.S. PATENT DOCUMENTS

| | | | |
|---|---|---|---|
| 2005/0113681 A1* | 5/2005 | DeFreitas | A61B 6/502 600/426 |
| 2008/0152077 A1* | 6/2008 | Ramsauer | A61B 6/502 378/37 |
| 2010/0111249 A1* | 5/2010 | Mertelmeier | A61B 6/025 378/37 |

FOREIGN PATENT DOCUMENTS

JP 2009136390 A 6/2009

* cited by examiner

*Primary Examiner* — Courtney Thomas
(74) *Attorney, Agent, or Firm* — Schiff Hardin LLP

(57) ABSTRACT

In a mammography apparatus, a deflection of an x-ray source aligned on a radiation detector is predetermined depending on the size of a breast compressed in the compression unit and/or the density of the breast tissue. Given an increasing deflection on an arc-shaped trajectory of the x-ray source, the compression of the breast is reduced at least once so that the path of the x-rays through the breast stays within a predetermined path length, starting from a first compression in a first x-ray acquisition.

14 Claims, 4 Drawing Sheets

MAMMOGRAPHY APPARATUS

BACKGROUND OF THE INVENTION

1. Field of the Invention

The invention concerns a mammography apparatus with a compression unit, and a method for operating such a mammography apparatus.

2. Description of the Prior Art

Mammography is an x-ray examination of the breast with the goal of detecting tissue variations at an optimally early stage. By continuous improvement of the mammography method it is sought to generate x-ray images with high significance in order to differentiate benign tissue variations from malignant tissue variations. In conventional x-ray mammography, a single two-dimensional image of a breast is generated at a single projection direction. A disadvantage of such imaging is that, due to overlapping tissue layers, it is often very difficult to detect a malignant structure in the region of a breast tissue. In order to obtain a three-dimensional image of the breast tissue, a number of x-ray images of the breast are acquired from respectively from different projection directions. During the x-ray acquisitions, the breast is fixed in position and simultaneously compressed in a compression unit. With these x-ray acquisitions, a three-dimensional image data set is generated via an image reconstruction algorithm (also called a tomosynthesis algorithm). For example, this three-dimensional image data set includes a number of slice images respectively situated parallel to the surface of the x-ray detector. Tissue structures situated atop one another in the propagation direction of the x-ray beam can be detected with this image data set. For tomosynthesis, x-ray exposures of the breast are acquired in a limited angle range of, for example, +/−25 degrees, starting from an orthogonal line established at the x-ray detector. Due to the incomplete scanning that results from this—i.e. due to the x-ray images being acquired only from a limited angle range of the breast—reconstruction of a plane from the 3D image data set has only a limited resolution. The resolution in the direction of the central beam (known as the depth resolution) is reduced relative to the resolution in the planes orthogonal to this direction.

SUMMARY OF THE INVENTION

An object of the present invention is to provide a mammography apparatus that achieves an improved image quality compared to the above-described conventional techniques.

The above object is achieved in accordance with the present invention by a mammography apparatus, and a method for operating a mammography apparatus, wherein a deflection of the x-ray source thereof, aligned on a radiation detector, is predetermined depending on the size of the breast that is compressed in the compression unit of the apparatus, and/or on the density of the breast tissue. Given an increasing deflection of the x-ray source on an arc-shaped trajectory of the x-ray source, the compression of the breast is reduced at least once, so that the path of the x-rays through the breast stays within a predetermined path length, starting from a first compression in a first x-ray acquisition of a number of projection acquisitions that are implemented as the x-ray source moves along the arc-shaped trajectory.

In the mammography apparatus according to the invention, the x-ray source is moved on a trajectory, a compression unit is provided to compress the breast, and a detector unit forms x-ray images, and an evaluation/monitoring unit is provided that predetermines a compression of the breast such that the distance that the x-rays travel through the breast tissue is minimized.

The invention has the advantage that the scatter radiation during an x-ray acquisition is reduced.

The invention also has the advantage that the depth resolution of a 3D x-ray image data set is improved due to a larger selectable angle range.

The invention has the advantage that the distances traveled by the x-rays through the breast are approximately the same given different alignment angles of the x-ray source on the breast.

The invention has the advantage that additional x-ray exposures of the breast are acquired in a second angle range, and—with the x-ray exposures acquired in a first angle range—are computed into a 3D image data set so that malignant breast tissue and/or micro-calcification can be better depicted.

DESCRIPTION OF THE PREFERRED EMBODIMENTS

Among other things, with the mammography apparatus according to the invention the compression of the breast tissue is predetermined depending on the dimensions of the breast and/or the density of the breast tissue, such that, in the case of (for example) an arc-shaped trajectory of the x-ray source aligned on the detector, the path of the x-rays (for example of the central beam of an x-ray cone) through the breast remains within a predeterminable deviation at different positions of the x-ray source along the trajectory. The compression exerted on the breast by the compression unit is predetermined to achieve and is constantly checked. In the figures, it is described when a conventionally standardized compression exerted on the breast is adapted individually to the patient in the course of an x-ray examination. A first patient-specific adjustment of the compression pressure can take place directly after the overview acquisition, as described in FIGS. 1, 2 and 3. A variation of the compression pressure on the breast can take place with a one-time adjustment or a continuous variation of the spacing between the first compression element and second compression element. The reduction of the compression on the breast can also take place as described in FIG. 4, within definable first and/or second angle ranges EB, ZB.

Figure 1:
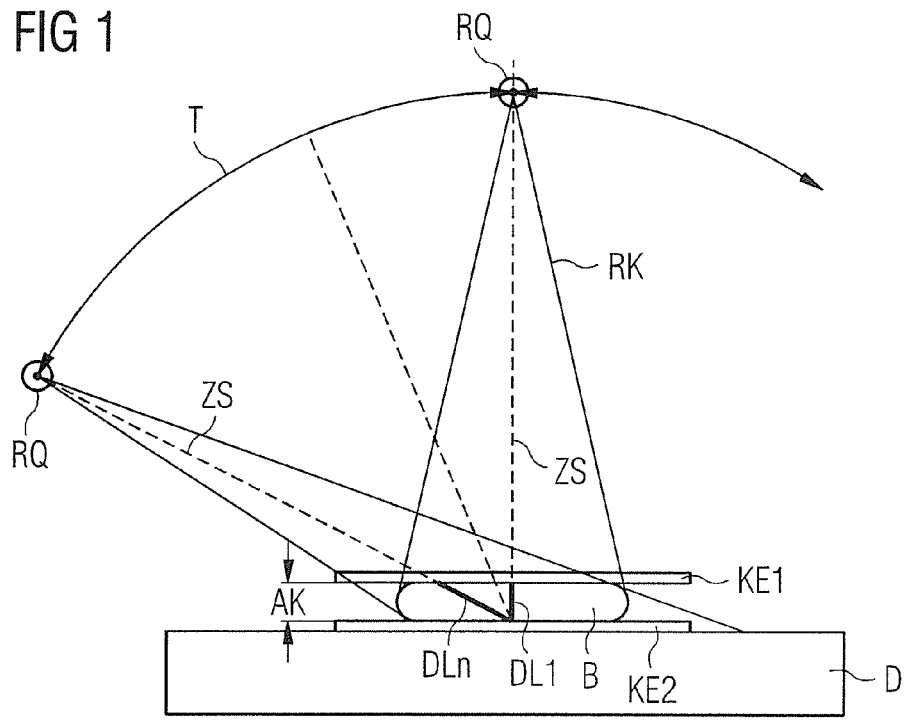
FIG. 1 is a schematic depiction of a first embodiment of a mammography apparatus according to the invention.
Figure 2:
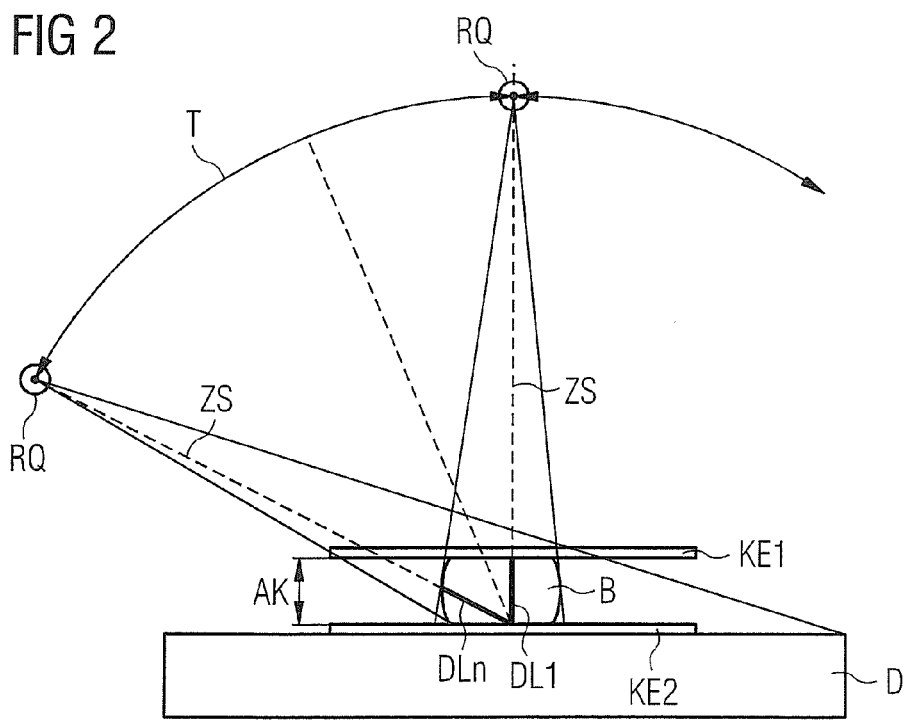
FIG. 2 is a schematic depiction of a second embodiment of a mammography apparatus according to the invention.

FIGS. 1 and 2 schematically show an x-ray source RQ that is moved on a trajectory T, an x-ray detector D, and a breast B compressed between first and second compression element KE1, KE2. The compression element KE2 can also be the detector housing or the detector cover.

In FIG. 1, the breast B is compressed by a standardized compression force. Here a first radioscopy path DL1 of the central beam ZS of an x-ray cone RK through the breast B is schematically shown given a 0 degree deflection of the x-ray source RQ. A possible n-th radioscopy path DLn given a greater deflection of the x-ray source RQ is also depicted. Given this present deflection of the x-ray source RQ, the path of the x-rays through the breast B is markedly longer than for the position of the x-ray source at 0 degrees.

Figure 3:
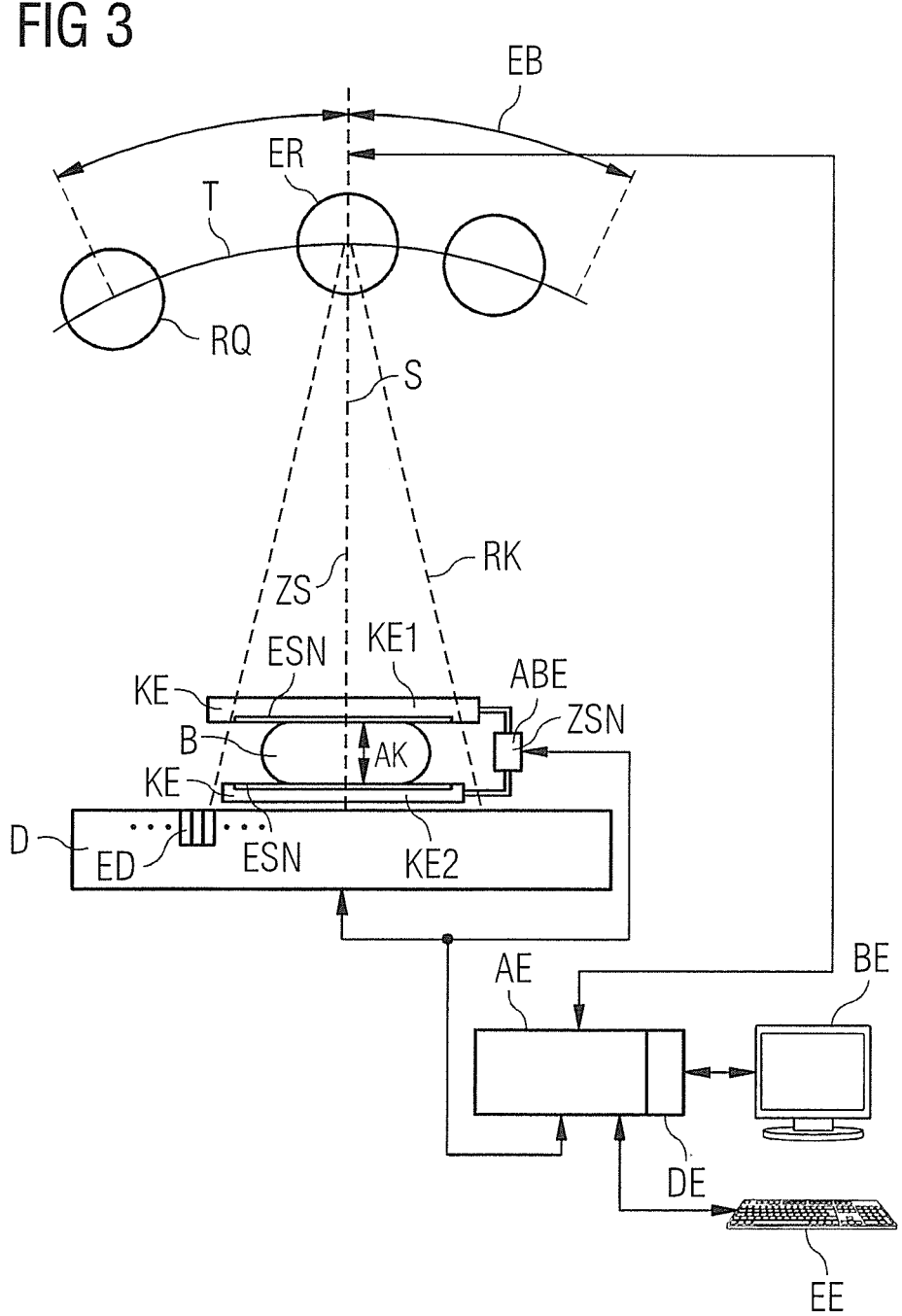
FIG. 3 shows a mammography apparatus with an indicated sequence of x-ray acquisitions within a first angle range according to the invention.

A first x-ray exposure or overview x-ray exposure ER, implemented at the position of the x-ray source RQ at 0 degrees, is relayed for an image analysis to be implemented in the evaluation unit AE (see FIG. 3). In the evaluation unit AE, the size of the breast B is determined by segmentation and/or first and second sensor data ESN, ZSN and/or the density is determined by an image analysis of the breast. Based on the detected and determined values as well as the spacing AK between the first and second compression elements KE1, KE2, a maximum possible deflection of the x-ray source RQ that is matched to the dimensions of the x-ray detector D is determined under consideration of a path length of the x-rays through the breast, which path length is to be minimized. An evaluation with regard to possible radioscopy paths DL'n through the breast B is additionally made at different compressions of the breast. If, based on the evaluation, x-ray path through the breast exist that exceeds an initially-determined path by a multiple of n, the compression is reduced as shown in FIG. 2. The reduction of the compression of the breast B can take place in one step or step-by-step. The compression pressure on the breast B results in a patient-specific manner. Based on an individual or joint evaluation of the spacing AK, the size of the breast, the density and the compression pressure during the first x-ray acquisition ER, the evaluation unit AE can determine the compression pressure for the breast at the individual x-ray acquisitions that are applied along the trajectory.

As indicated above, the compression of the breast B is predetermined by the evaluation unit AE with the goal that the radioscopy path DLx through the breast does not differ by a multiple of n from a radioscopy path determined at the beginning of the x-ray examination, even given larger angle positions of the x-ray source RQ on the arc-shaped trajectory.

FIG. 3 shows an exemplary embodiment of a mammography apparatus to create x-ray exposures for a 3D x-ray image data set. The x-rays generated by the x-ray source RQ arrive at the x-ray detector D within an x-ray cone RK. The x-rays emanating from the x-ray source RQ are received by a large-area x-ray detector D (made up of a plurality of individual detectors ED arranged in a matrix-like array) and converted into visible images. The compression unit KE depicted here is formed from the first and second compression elements KE1, KE2. The first and second compression elements KE1, KE2 are adjustable in terms of their height. After an adaptation of the height of the second compression element KE2 to the anatomy of the respective patient, the first compression element KE1 is lowered in a controlled manner in the direction of the second compression element KE2, and the breast of the patient is fixed or compressed. The adjustments and positioning of the x-ray source RQ and the compression values of the compression unit KE are controlled by evaluation, control and safety modules arranged in the monitoring/evaluation unit AE. With the aid of input and display elements (reasonably illustrated in the example by an input unit EE and a monitor unit BE) the acquisition parameters provided to generate individual projection images can be adjusted by the user or, in the event that these are predetermined by the control or, respectively, evaluation unit, can be reviewed and modified specifically to the patient as necessary. In this depiction, the trajectory T is formed in an arc or circle shape. The x-ray source RQ moves along this trajectory T. Respective x-ray beams can be triggered at predeterminable angle positions. The respective x-ray images are read out from the x-ray detector D and computed to form a 3D image data set. An orthogonal S is indicated on the detector surface. In this depiction, the central beam ZS of the x-ray cone RK also lies on this orthogonal S. In this presentation, the x-ray source RQ moves along the trajectory T within a first angle range EB. Starting from the orthogonal S at 0°, the first angle range EB extends to both sides of this. For example, an angle range from 0 to 50 degrees can be predetermined for the first angle range EB. As already described above, the first angle range EB is predetermined specifically for the patient by the density and/or the size of the breast B. The density of the breast tissue and/or the size of the breast is respectively determined by means of an overview x-ray exposure ER. As an overview x-ray exposure, the first x-ray exposure can also be used to create the 3D image data set. At this point in time the breast is fixed between the compression elements KE1, KE2 with a compression pressure matched to the breast of the patient. For example, a first angle range EB is rendered more precisely using the imaging brightness of the breast tissue in the overview x-ray image RE and the dimensions of the breast and/or the spacing of the compression element. The dimensions of the breast are determined by first and second sensors ESN, ZSN in the first and second compression elements KE1, KE2. If an average image brightness of the breast tissue is present in the overview image x-ray image ER, the first angle range EB is provided for the maximum deflection of the x-ray source in this first angle range EB, for example. Given a low image brightness of the breast tissue, the first angle range EB can be reduced, for example. Given an increased image brightness of the breast tissue, an increased density of the breast tissue can be concluded and a larger first angle range EB can be provided.

In addition, the density of the breast tissue can also be determined via sensors. For this, as stated above the size of the breast B can be determined with (for example) first sensors ESN on and/or in the first and second compression elements KE1, KE2 in connection with second sensors ZSN in a second distance measurement unit ABS between the first and second compression element KE1, KE2. These measurement data of the first and/or second sensors ESN, ZSN can additionally be evaluated in combination with pressure-sensitive measurement data that have been acquired during the fixing and compression phase to create the overview x-ray image.

The density can also be determined computationally from the overview x-ray image or in an image-based manner.

The radioscopy path (for example of the central beam ZS) can be calculated based on the density determination and the dimensions of the compressed breast. The density of the breast tissue is determined in a tissue density determination unit DE associated with the monitoring/evaluation unit AE.

Figure 4:
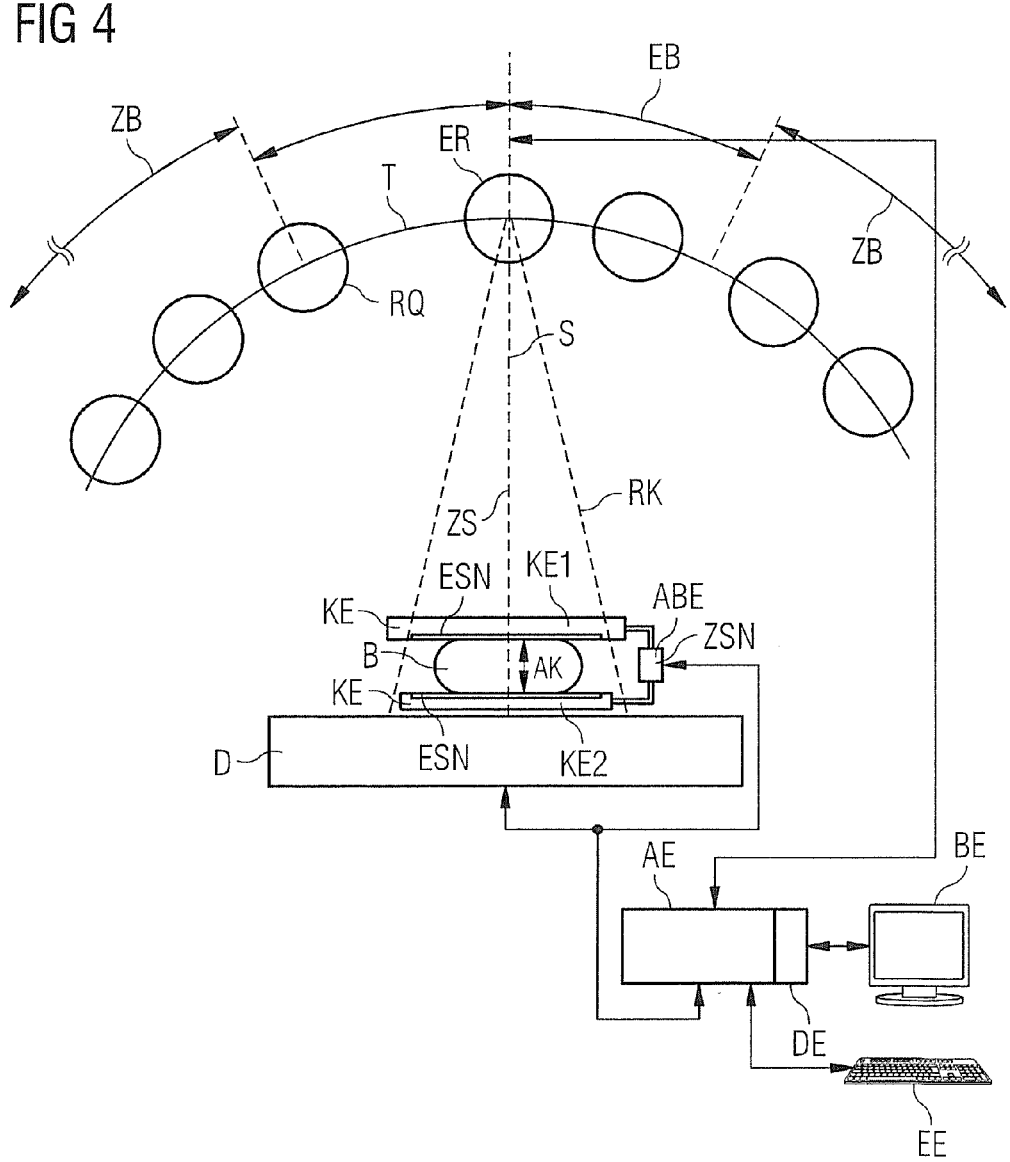
FIG. 4 shows a mammography apparatus with a second angle range according to the invention.

In FIG. 4, the mammography apparatus schematically presented in FIG. 3 is supplemented with a second angle range ZB along the indicated trajectory T. The compression of the breast B is constant in the first angle range EB. The compression of the breast B can take place by means of a compression executed in a standardized manner. A patient-specific compression of the breast is likewise possible in the first angle range EB. According to the invention, a largest possible angle range ZB is added to the first angle range E under consideration of the breast size and/or the breast density under simultaneous reduction of the compression on the breast. The reduction of the compression in the second angle range can take place with one step or step-by-step in multiple steps, or continuously. Together, the first and second angle ranges EB, ZB should be greater than 50 degrees on both sides of the orthogonal S. The expanded scanning of the breast that is achieved can likewise be designated as a wide angle tomosynthesis. This procedure has the advantage that the x-rays travel approximately the same path through the breast at each position of the x-ray source during the sequence of x-ray acquisitions. This has the advantage that the attenuation of the x-ray beam through the breast tissue is approximately the same, and the scatter radiation does not increase in larger angle ranges. The invention thus has the further advantage that additional x-ray exposures of the breast are acquired in this angle range and computed with the x-ray exposures acquired in the first angle range, and thus malignant tissue and/or micro-calcifications can be depicted in an improved manner.

Depending on the density of the breast tissue and/or the size of the breast, as well as the spacing between the first and second compression elements KE1, KE2, first and second angle ranges EB, ZB are provided by the evaluation unit AE while maintaining a previously executed compression on the breast. During the progress of the x-ray source on the trajectory T, the spacing AK can already be increased in the first angle range. The spacing AK can be further increased in the second angle range ZB. This spacing between the first and second compression elements KE1, KE2 increases in such a manner that the compression of the breast is withdrawn so that the original shape of the breast can reform.

Assuming an average breast density, the breast can be pressed with a force of between 50 and 100 newtons during the compression phase. In special cases, these values can be deviated from depending on patient constitution. According to the invention, the pressure on the breast tissue is reduced after a compression phase (as discussed above) at a first x-ray acquisition ER. The compression of the breast is reduced by the evaluation and monitoring unit AE in such a manner that the path that the x-ray beam travels through the breast tissue does not become n-times longer or remains below a predeterminable deviation given progress of the x-ray source RQ on the trajectory T.

In one embodiment of the mammography apparatus, the compression can be continuously reduced (as described above) beginning at a maximum compression at the 0 degree position of the x-ray source RQ if the x-ray source RQ is moved through the first and second angle range along the trajectory T.

Figure 5:
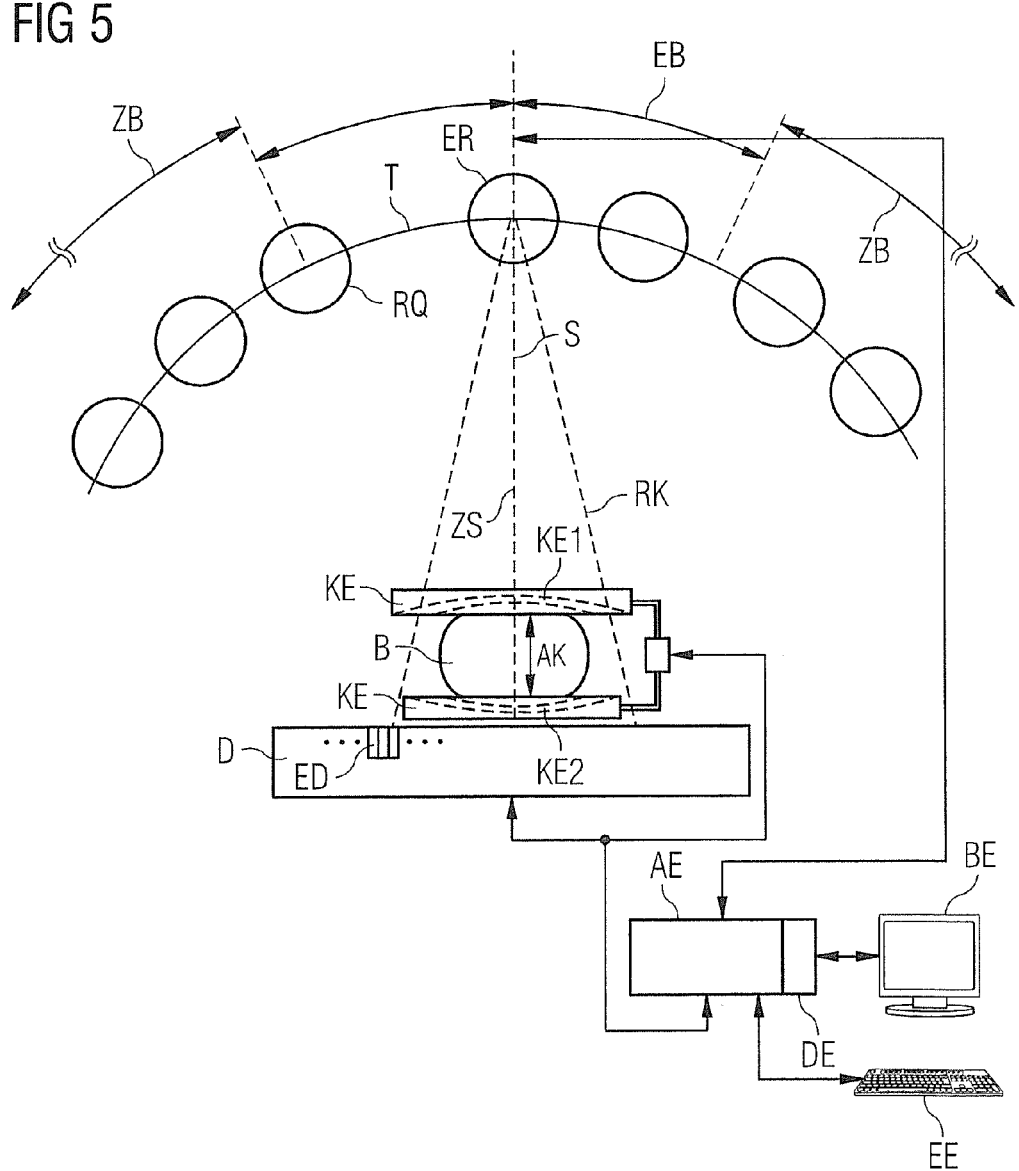
FIG. 5 shows an additional embodiment according to the invention.

Given the mammography apparatus schematically depicted in FIG. 5, the insides of the first and second compression elements KE1, KE2 of the compression unit KE are respectively fashioned to be slightly curved. Two variants of a curved inside of the first and second compression elements KE1, KE2 are indicated in FIG. 5. In this embodiment, the first compression element KE1 can be curved or concave, and in contrast to this the second compression element KE2 can have a recess to accommodate the breast.

The first compression element KE1 can likewise be formed by a compression band, with tensioning devices arranged in the edge region of the second compression element KE2.

Although modifications and changes may be suggested by those skilled in the art, it is the intention of the inventors to embody within the patent warranted hereon all changes and modifications as reasonably and properly come within the scope of their contribution to the art.

We claim as our invention:

1. A mammography apparatus comprising:
an x-ray source that emits an x-ray beam that comprises a central ray;
a compression unit that compresses a breast therein with an adjustable compression pressure;
a radiation detector;
said x-ray source being mounted for movement along an arc-shaped trajectory so as to irradiate the breast in the compression unit with said x-ray beam from each of a plurality of different projection angles along said arc-shaped trajectory, and said radiation detector detecting x-rays that have proceeded through the breast in the compression unit at each of said projection angles, with said central ray proceeding through a different radioscopy path in the breast at the respective projection angles; and
a control and evaluation unit configured to adjust the compression pressure applied to the breast by said compression unit to cause said radioscopy path of said central ray through the compressed breast to stay within a predetermined deviation, relative to a length of said radioscopy path at a first of said projection angles, as said x-ray source proceeds through said different projection angles along said arc-shaped trajectory.

2. A mammography apparatus as claimed in claim 1 wherein said control and evaluation unit receives sensor data selected from the group consisting of sensor data that designate a size of the breast and sensor data that designate a spacing between compression elements of said compression unit when said breast is compressed in said compression unit, said control and evaluation unit being configured to specify said compression pressure for each of said projection angles from said sensor data, dependent on said sensor data received with said x-ray source at said first of said projection angles.

3. A mammography apparatus as claimed in claim 2 wherein said control and evaluation unit is configured to establish a first angle range and a second angle range along said arc-shaped trajectory, dependent on said sensor data, and to reduce said compression pressure, at least in one of said first angle range or said second angle range, to cause said radioscopy path of said central ray through the breast to not exceed a predetermined path length.

4. A mammography apparatus as claimed in claim 1 wherein said x-ray source is configured to provide an overview x-ray exposure of the breast to said control and evaluation device, and wherein said control and evaluation device is configured to determine, from said overview x-ray exposure of the breast, tissue density of the breast, and to use said tissue density to specify said compression pressure.

5. A mammography apparatus as claimed in claim 4 wherein said control and evaluation unit is configured to establish a first angle range and a second angle range along said arc-shaped trajectory, dependent on said tissue density, and to reduce said compression pressure, at least in one of said first angle range or said second angle range, to cause said radioscopy path of said central ray through the breast to not exceed a predetermined path length.

6. A mammography apparatus as claimed in claim 1 wherein said evaluation unit is configured to receive sensor data, selected from the group consisting of sensor data that designate a size of the breast and sensor data that designate a spacing between first and second compression elements of said compression unit given a compressed breast in the compression unit, while said x-ray source is situated at each of said projection angles, and wherein said x-ray source is configured to provide an overview x-ray exposure of the breast in the compression unit to said control and evaluation unit and wherein said control and evaluation unit is configured to analyze said overview x-ray exposure to determine a tissue density of the breast in said compression unit, and wherein said control and evaluation unit is configured to determine said compression pressure dependent on said tissue density, and dependent on said sensor data received with said x-ray source at said first of said projection angles.

7. A mammography apparatus as claimed in claim 6 wherein said control and evaluation unit is configured to establish a first angle range and a second angle range along said arc-shaped trajectory, dependent on said sensor data, and to reduce said compression pressure, at least in one of said first angle range or said second angle range, to cause said radioscopy path of said central ray through the breast to not exceed a predetermined path length.

8. A method for operating a mammography apparatus comprising:
  operating an x-ray source to emit an x-ray beam that comprises a central ray;
  with a compression unit, compressing a breast with an adjustable compression pressure;
  moving said x-ray source along an arc-shaped trajectory and irradiating the breast in the compression unit with said x-ray beam from each of a plurality of different projection angles along said arc-shaped trajectory and, with a radiation detector detecting x-rays that have proceeded through the breast in the compression unit at each of said projection angles, with said central ray proceeding through a different radioscopy path in the breast at the respective projection angles; and
  from a control and evaluation unit, adjusting the compression pressure applied to the breast by said compression unit to cause said radioscopy path of said central ray through the compressed breast to stay within a predetermined deviation, relative to a length of said radioscopy path at a first of said projection angles, as said x-ray source proceeds through said different projection angles along said arc-shaped trajectory.

9. A method as claimed in claim 8 comprising providing said control and evaluation unit with sensor data selected from the group consisting of sensor data that designate a size of the breast and sensor data that designate a spacing between compression elements of said compression unit when said breast is compressed in said compression unit, and in said control and evaluation unit, specifying said compression pressure for each of said projection angles from said sensor data, dependent on said sensor data received with said x-ray source at said first of said projection angles.

10. A method as claimed in claim 9 comprising in said control and evaluation unit, establishing a first angle range and a second angle range along said arc-shaped trajectory, dependent on said sensor data, and reducing said compression pressure, at least in one of said first angle range or said second angle range, to cause said radioscopy path of said central ray through the breast to not exceed a predetermined path length.

11. A method as claimed in claim 8 comprising operating said x-ray source to provide an overview x-ray exposure of the breast to said control and evaluation device, and, in said control and evaluation device, determining, from said overview x-ray exposure of the breast, tissue density of the breast, and using said tissue density to specify said compression pressure.

12. A method as claimed in claim 9 comprising in said control and evaluation unit, establishing a first angle range and a second angle range along said arc-shaped trajectory, dependent on said tissue density, and reducing said compression pressure, at least in one of said first angle range or said second angle range, to cause said radioscopy path of said central ray through the breast to not exceed a predetermined path length.

13. A method as claimed in claim 8 comprising providing said evaluation unit with sensor data, selected from the group consisting of sensor data that designate a size of the breast and sensor data that designate a spacing between first and second compression elements of said compression unit given a compressed breast in the compression unit, while said x-ray source is situated at each of said projection angles, and operating said x-ray source to provide an overview x-ray exposure of the breast in the compression unit to said control and evaluation unit and in said control and evaluation unit, analyzing said overview x-ray exposure to determine a tissue density of the breast in said compression unit, and determining said compression pressure dependent on said tissue density, and dependent on said sensor data received with said x-ray source at said first of said projection angles.

14. A method as claimed in claim 13 comprising, in said control and evaluation unit, establishing a first angle range and a second angle range along said arc-shaped trajectory, dependent on said sensor data, and reducing said compression pressure, at least in one of said first angle range or said second angle range, to cause said radioscopy path of said central ray through the breast to not exceed a predetermined path length.

* * * * *